United States Patent [19]

Machinami et al.

[11] Patent Number: 4,889,926
[45] Date of Patent: Dec. 26, 1989

[54] METHOD FOR THE SYNTHESIS OF (2"R)-4'-O-TETRA-HYDROPYRANYLA-DRIAMYCIM USING 14-CHLORO-DAUNOMYCIN AS AN INTERMEDIATE

[75] Inventors: Tomoya Machinami, Yokosuka; Takeshi Nakamura, Yokohama; Ken Nishihata, Yokohama; Shinichi Kondo, Yokohama; Tomio Takeuchi, Tokyo, all of Japan

[73] Assignee: Zaidan Hojin Biseibutsu Kagaku Kenkyu Kai, Tokyo, Japan

[21] Appl. No.: 204,363

[22] Filed: Jun. 9, 1988

[30] Foreign Application Priority Data

Jun. 12, 1987 [JP] Japan .................................. 62-145339
Jul. 14, 1987 [JP] Japan .................................. 62-173924

[51] Int. Cl.$^4$ ............................................ C07H 15/24
[52] U.S. Cl. ..................................................... 536/6.4
[58] Field of Search ............................................ 536/6.4

[56] References Cited

U.S. PATENT DOCUMENTS 4,818,818 4/1989 Umezawa et al. .................... 536/6.4

Primary Examiner—Joseph L. Schofer
Assistant Examiner—Gary L. Kunz
Attorney, Agent, or Firm—Larson and Taylor

[57] ABSTRACT

A new compound, i.e., 14-chlorodaunomycin, and its method of preparation are provided. The new compound, useful as an antitumor agent and as an intermediate in the preparation of (2"R)-4'-O-tetrahydropyranyladriamycin, is obtained by reaction of daunomycin with an alkyl ortho-formate and a brominating agent to produce a 14-bromo-13-dialkylketaldaunomycin, hydrolysis of the latter compound, then adding an excess of a solid metal/chloride to produce an acid addition salt of 14-chlorodaunomycin and concurrently salting out the latter compound from the reaction solution, followed by recovering the 14-chlorodaunomycin acid addition salt.

7 Claims, No Drawings

METHOD FOR THE SYNTHESIS OF (2''R)-4'-O-TETRA-HYDROPYRANYLA-DRIAMYCIM USING 14-CHLORO-DAUNOMYCIN AS AN INTERMEDIATE

SUMMARY OF THE INVENTION

This invention relates to a new compound, 14-chlorodaunomycin and acid addition salts thereof, which themselves have antitumor activity and are useful as antitumor agent and also useful as intermediate compounds for the production of semi-synthetic antibiotics of anthracycline type valuable as antitumor agent. This invention also relates to an efficient to an efficient process for the preparation of 14-chlorodaunomycin. This invention further relates to a new and efficient process for the preparation of (2''R)-4'-O-tetrahydropyranyladriamycin, which is one of the antitumor agents of the semi-synthetic anthracycline derivative-type.

14-Chlorodaunomycin according to this invention is the compound of formula (I)

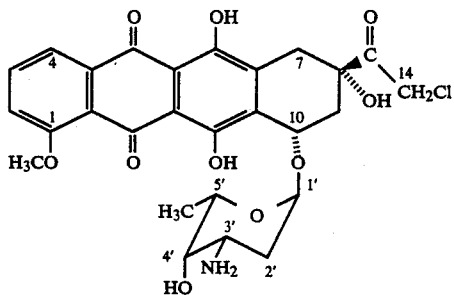

This new compound of formula (I) is useful as an important intermediate product for use in the synthesis of the (2''R)-4'-O-tetrahydropyranyladriamycin of formula (A)

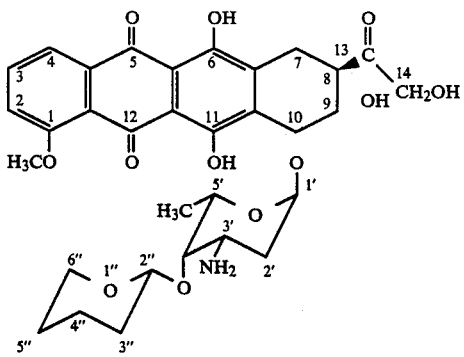

which is practically effective in the therapeutic treatment of tumor-bearing patients.

BACKGROUND OF THE INVENTION

That 4'-O-tetrahydropyranyladriamycin has antitumor activity is disclosed in Japanese patent publication No. 47194/81 and the U.S. Pat. No. 4,303,785.

The known processes for the preparation of (2''R)-4'-O-tetrahydropyranyladriamycin of formula (A) shown above, which employ daunomycin of formula (II)

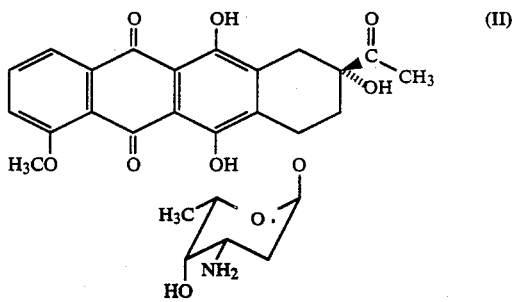

as the starting compound, include the process as disclosed in Japanese patent application first publication "Kokai" No. 156,300/81, U.S. Pat. No. 4,360,664 and European patent application No. 39,060-Al, as well as the process as disclosed in Japanese patent application first publication "Kokai" No. 104,299/80, U.S. Pat. No. 4,303,785 and European patent application No. 14,853-Al. According to the first-mentioned process of Japanese patent application first publication "Kokai" No. 156,300/81 or U.S. Pat. No. 4,360,664 (2''R)-4'-O-tetrahydropyranyladriamycin (hereinafter sometime abbreviated as (2''R)-4'-O-THPADM) of the formula (A) is produced by brominating daunomycin (hereinafter sometime abbreviated as DM) of the formula (II) in the presence of methyl orthoformate, then treating hydrolytically the resulting reaction product, and by-produced 14-bromo-13-dimethylketaldaunomycin of formula (IV')

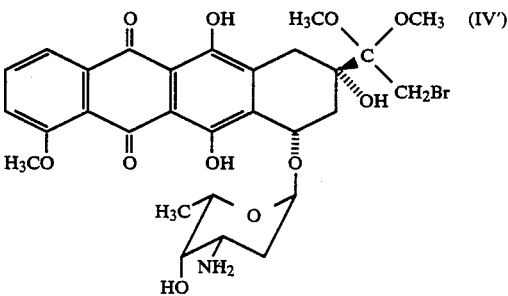

with acetone and water, to produce 14-bromodaunomycin of formula (V)

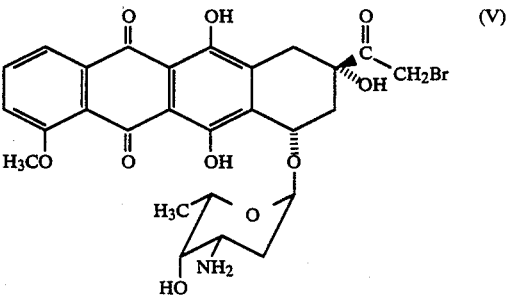

and subsequently 4'-O-tetrahydropyranylating the 14-bromodaunomycin of formula (V) by reaction with 3,4-dihydro-2H-pyran, then hydrolyzing the resulting 14-bromo-4'-O-tetrahydropyranyldaunomycin and the otherwise -O-tetrahydropyranylated by-products to produce the 4'-O-tetrahydropyranyladriamycin and the other hydrolyzed by-products, and finally separating the desired (2″R)-4′-O-THPADM from the undesired by-products through a column chromatography to recover the (2″R)-4′-O-THPADM. While, according to the second-mentioned process of the Japanese patent application first publication "Kokai" No. 104,299/80 or U.S. Pat. No. 4,303,785, (2″R)-4′-O-THPADM of formula (A) is produced by converting 14-bromodaunomycin of formula (V) into 14-acetoxydaunomycin of formula (B)

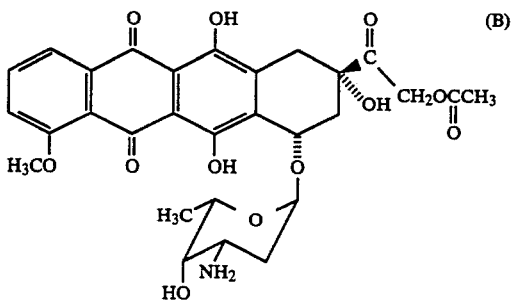

and then 4′-O-tetrahydropyranylating 14-acetoxydaunomycin, subsequently hydrolyzing the resulting 4′-O-tetrahydropyranyl-14-acetoxydaunomycin and the otherwise O-tetrahydropyranylated by-products to produce the 4′-O-tetrahydropyranyladriamycin and the other hydrolyzed by-products, and finally separating the desired (2″R)-4′-O-THPADM from the undesired by-products through a column chromatography for recovery and purification of the desired (2″R)-4′-O-THPADM product, with the aforesaid 4′-O-tetrahydropyranylation, the subsequent hydrolysis and the chromatographic separation of the (2″R)-4′-O-THPADM being conducted in the same manner as in the first-mentioned process of the Japanese patent application first publication "Kokai" No. 156,300/81 or U.S. Pat. No. 4,360,664. Incidentally, the absolute chemical structure of (2″R)-4′-O-THPADM of formula (A) described in the present invention has been determined by an X-ray analysis of a certain derivatives of (2″R)-4′-O-THPADM [see Hamao Umezawa et al., "Journal of Antibiotics" 37, 1094–1097 (1984)]. As the method for the preparation of (2″R)-4′-O-THPADM starting from adriamycin, there has been known another method as disclosed in U.S. Pat. No. 4,303,785 or in Japanese Patent Publication No. 47,194/81 and Japanese patent application first publication "Kokai" No. 116,591/87, U.S. Patent application Ser. No. 925,774 or European patent application publication No. 228,546-A2.

In the known processes for the preparation of (2″R)-4′-O-THPADM with employing DM as a starting compound, such intermediate compound where the tetrahydropyranyl group as introduced to the 4′-position of DM shows the desired (2″R)-configuration can be formed in the 4′-O-tetrahydropyranylation step. With these known processes, however, it is then impossible to avoid the by-formation of such compound where the 4′-O-tetrahydropyranyl group has the (2″S)-configuration, as a stereoisomer, and also the by-formation of such 9,4′-di-O-tetrahydropyranylated compounds due to that the tetrahydropyranylation has taken place not only at the 4′-position but also at the 9-position of DM. The yield of the desired (2″R)-4′-O-THPADM must therefore be very low, as long as it is prepared with starting from DM.

As a measure for improving such low yield of the intended final product, it will be possible to resort on such a method in which the above-described two by-products, namely the (2″S)-4′-O-tetrahydropyranylated product and the 9,4′-di-O-tetrahydropyranylated products, are recovered and then converted into intermediate product suitable for their recycle and re-use in the synthesis of (2″R)-4′-O-THPADM. With the known two processes mentioned above, the 14-bromodaunomycin which is produced as the intermediate compound involved is unstable in its nature, and primarily due to this, it is not yet possible to provide and establish such a method which is suitable for the recovery, recycle and re-use of the by-products for the synthesis of the desired (2″R)-4′-O-THPADM.

We, the present inentors, have made extensive researches with a view toward exploiting and providing such an improved new process of preparing (2″R)-4′-O-THPADM, which can solve the problems of the low efficiency of the prior art processes mentioned above, by making the new process feasible to be conducted via an intermediate product of high stability, in which the desired (2″R)-4′-O-THPADM can be obtained from the main reaction product of the 4′-O-tetrapyranylation step of the process and concurrently the by-products as formed in the tetrahydropyranylation step can be recovered and converted back into the intermediate product of high stability in a high yield, and in which the highly stable intermediate product so recovered can be recycled and re-used for the synthesis of the desired final product, whereby the production of the desired (2″R)-4′-O-THPADM can be achieved in a high overall yield even when daunomycin (DM) is employed as the starting compound.

In the above-mentioned known processes for the preparation of (2″R)-4′-O-THPADM of formula (A) in which daunomycin (DM) of formula (II) is used as the starting compound, and which are effected via the 14-bromodaunomycin of formula (V) as the intermediate product (namely the processes of the aforesaid Japanese patent application first publication "Kokai" Nos. 104,299/80 and 156,300/81), there are formed great amounts of the undesired by-products in the tetrahydropyranylation step so that the intended final compound can be obtained only in a low yield with these prior art processes. The intermediate compound, 14-bromodaunomycin is so unstable that even when it has been stored in its solid state at −10° C. for about 1 week, 14-bromodaunomycin can remain only in such an amount which is as little as about two-thirds of its initial amount before its storage, due to that the amino sugar moiety bonded to the 7-position can be cleaved to bring about the degradation of 14-bromodaunomycin.

On the other hand, the known 14-halogenated derivatives of daunomycin include 14-iododaunomycin, in addition to the aforesaid 14-bromodaunomycin of formula (II). 14-Bromodaunomycin and 14-iododaunomycin are used as intermediate products which are important to produce adriamycin of formula (C)

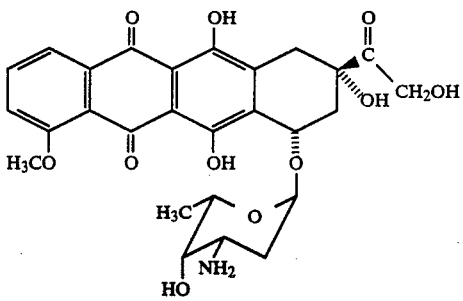

from daunomycin of formula (II) (see Japanese patent publication No. 46,597/72 or U.S. Pat. No. 3,803,124 for instance). 14-Bromodaunomycin may also be prepared by direct bromination of daunomycin (see the above-mentioned Japanese patent publication No. 46,597/72 or U.S. Pat. No. 3,803,124). A 14-iododaunomycin derivative which has been known hithertobefore is specifically 14-iodo-N-trifluoroacetyldaunomycin of formula (D)

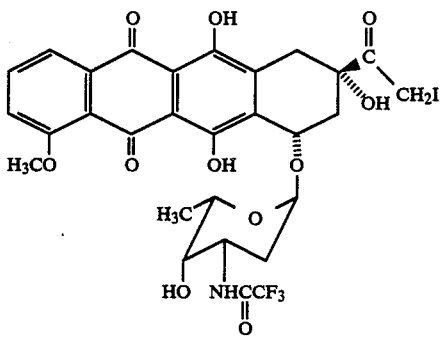

which is prepared by a method comprising reacting an N-trifluoroacetylated derivative of daunomycin with iodine in the presence of calcium oxide (see Japanese patent publication No. 46,597/72, for instance). The other 14-halogenated derivative of daunomycin is a 14-fluoro derivative of daunomycin which was synthesized only for the purpose of estimating its antitumor activity and which was reported by Terajima et al (see the "Kohen-Yo-shi-shu" for the fifty-fourth annual spring symposium of the "Japan Chemical Society" Vol. 3, III L 40). As far as we, the present inventors, are aware of 14-chlorodaunomycin is neither disclosed nor reported yet in any literatures.

In the course of our extensive researches in an attempt to provide an improved new process for the preparation of (2"R)-4'-O-THPADM of formula (A) as described in the above, we, the present inventors, have paid our attention on the utilizability of a chloro substituent which is more stable than the iodo group or the bromo group present in the 14-iododaunomycin or 14-bromodaunomycin as previously used as the intermediate compounds and which is not so unreactive as much as the fluoro group present in the 14-fluorodaunomycin, so that we have had an attempt to firstly produce 14-chlorodaunomycin as a new compound. As a result of our investigations, we have now succeeded in producing 14-chlorodaunomycin, and we have also succeeded in exploiting an efficient process for the preparation of 14-chlorodaunomycin. Thus, we have now found that when a series of reaction steps comprising the ketalation and bromination of DM in the presence of an alkyl orthoformate to produce a 14-bromo-14-dialkylketal-daunomycin of formula (IV), and the subsequent hydrolysis of the latter compound with an aqueous acid solution under acidic conditions to give an aqueous solution of 14-bromodaunomycin of formula (V) is carried out successively, and when a large amount of a metal halide, preferably, an alkali metal or alkaline earth metal halide is then added to said aqueous solution of 14-bromodaunomycin of formula (V), a halogen-interchange reaction takes place between the 14-bromo group of 14-bromodaunomycin of formula (V) and the metal halide and thus 14-chlorodaunomycin of formula (I) can be produced efficiently with its salting-out from the reaction solution taking place efficiently so that the production and isolation of 14-chlorodaunomycin are effected in a facile way, and also that 14-chlorodaunomycin is extremely more stable than 14-bromodaunomycin, and further that 14-chlorodaunomycin is useful as an intermediate for the synthesis of (2"R)-4'-O-THPADM of formula (A) and is stable enough to permit the recovery, recycle and re-use of 14-chlorodaunomycin.

We have also found that 14-chlorodaunomycin can be prepared from daunomycin in a high yield as the consequence of that the halogen-exchange reaction between 14-bromodaunomycin and a metal chloride to produce 14-chlorodaunomycin takes place efficiently and concurrently the reaction product, namely 14-chlorodaunomycin can be isolated efficiently from the reaction solution through its salting-out, as described in the above.

According to a first aspect of this invention, therefore, there is provided 14-chlorodaunomycin represented by formula (I)

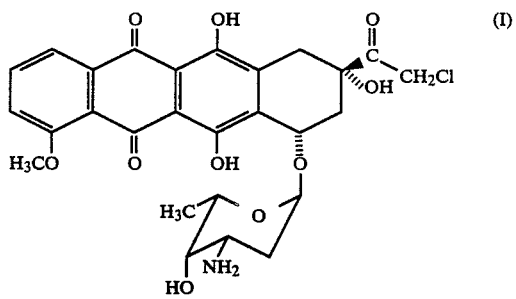

or an acid addition salt thereof.

The acid addition salt of 14-chlorodaunomycin includes a salt of 14-chlorodaunomycin with a pharmaceutically acceptable inorganic acid such as hydrochloric acid, sulfuric acid, phosphoric acid, nitric acid and hydrobromic acid, or with a pharmaceutically acceptable organic acid such as acetic acid, propionic acid, maleic acid, citric acid, succinic acid and methanesulfonic acid.

According to the second aspect of this invention, there is provided a process for the preparation of 14-chlorodaunomycin of formula (I)

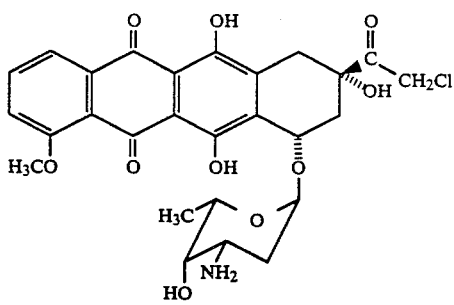

or an acid addition salt thereof, which comprises reacting daunomycin of formula (II)

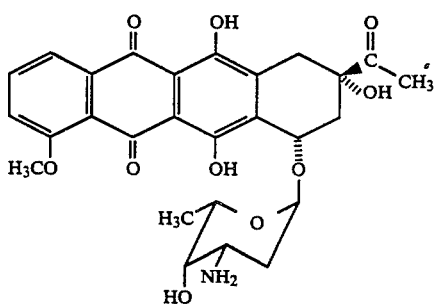

or an acid addition salt thereof with an alkyl orthoformate of formula (III)

CH(OR)₃                                                                                                       (III)

wherein R is a lower alkyl group, and a brominating agent in solution in an organic solvent to form a 14-bromo-13-dialkylketaldaunomycin of formula (IV)

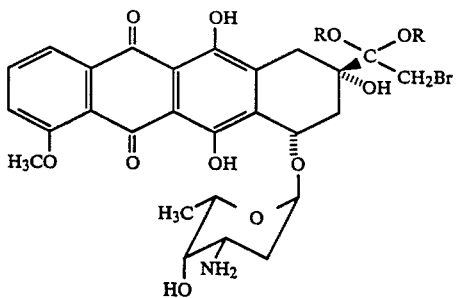

wherein R is as defined above, or an acid addition salt thereof, hydrolyzing the compound of formula (IV) by treating with an aqueous solution of an acid under acidic conditions, then adding an excess amount of a solid metal chloride to the resulting aqueous reaction mixture containing the acid-addition salt of 14-bromodaunomycin so produced and represented by formula (V)

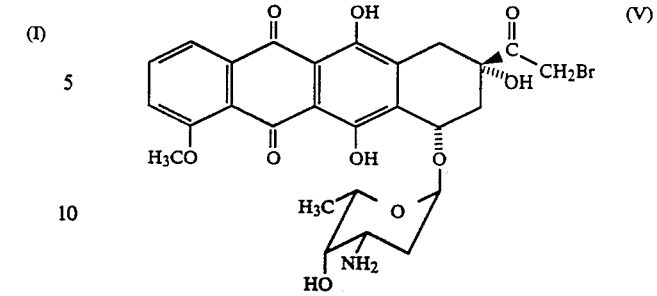

to dissolve the solid metal chloride into said aqueous reaction mixture and to react the dissolved metal chloride with the 14-bromodaunomycin acid-addition salt so that the 14-bromo group of 14-bromodaunomycin of formula (V) undergoes the halogen-exchange reaction with the metal chloride to produce the acid-addition salt of 14-chlorodaunomycin of formula (I) and concurrently allowing the acid-addition salt of the 14-chlorodaunomycin of formula (I) to be precipitated from the resulting aqueous reaction solution by the salting-out of the 14-chlorodaunomycin acid-addition salt, and recovering the acid-addition salt of 14-chlorodaunomycin from the aqueous reaction solution, and when desired, treating the recovered 14-chlorodaunomycin acid-addition salt with an aqueous compound under weakly alkaline conditions to afford 14-chlorodaunomycin in its free base form.

In the process according to the second aspect of this invention, the starting daunomycin of formula (II) may be used in its free base form or as an acid addition salt (preferably the hydrochloride) thereof, and the starting daunomycin is reacted with excessive amounts of an alkyl orthoformate of formula (III) and a brominating agent such as bromine, pyridinium hydrobromide perbromide, pyrrolidone hydrotribromide, and phenyltrimethylammonium perbromide. As illustrative examples of the alkyl orthoformate of formula (III) employed in the above process, may be mentioned lower ($C_1$–$C_6$) alkyl orthoformates such as methyl orthoformate and ethyl orthoformate. In this way, both the ketalation and bromination of DM take place to give the 14-bromo-13-dialkylketaldaunomycin of formula (IV). The desirable reaction temperature of these reactions may range from 0° C. to 30° C., while the preferable reaction time may range from 30 minutes to 4 hours.

The 14-bromo-14-dialkylketaldaunomycin of the formula (IV) obtained by the above reactions is then hydrolytically treated with an aqueous solution of an acid (eg, hydrobromic acid) in an inert organic solvent. It is desirable to conduct this hydrolysis reaction at a reaction temperature of 0°–50° C. for 1–48 hours. As illustrative examples of the inert organic solvent mentioned above, may be mentioned alcohols such as methanol and ethanol, ketones such as acetone, and ethers such as tetrahydrofuran, dioxane and dimethoxyethane. Illustrative examples of the acid which are useful for the hydrolysis may include strong mineral acids such as hydrochloric acid, hydrobromic acid, sulfuric acid and phosphoric acid, as well as strong organic acids such as organic sulfonic acids, e.g., methanesulfonic acid and toluenesulfonic acid. From the resulting water-containing reaction mixture containing the acid-addition salt of 14-bromodaunomycin so produced is removed the organic solvent phase, and to the resultant aqueous solution of 14-bromodaunomycin is added a large amount of a metal chloride in a solid form. The large amount of the solid metal chloride is dissolved in the water-containing reaction mixture and the dissolved metal chloride is reacted with 14-bromodaunomycin to produced 14-chlorodaunomycin, which is then salted-out from the reaction solution due to the presence of the large amount of the metal chloride as dissolved in the reaction solution, whereby 14-chlorodaunomycin hydrochloride precipitates. The precipitate is then collected and dried, thereby affording 14-chlorodaunomycin hydrochloride as powder. As exemplary metal chlorides which are useful in the above halogen-exchange reaction, may be mentioned not only the chlorides of alkali metals such as lithium, sodium and potassium but also the chlorides of alkaline earth metals such as barium. The excess amount of the solid metal chloride added to the aqueous reaction mixture containing the 14-bromodaunomycin acid addition salt produced may be such amount of the metal chloride that a part of the metal chloride as dissolved from the added solid metal chloride into said aqueous reaction mixture is sufficient to convert all the 14-bromodaunomycin present into the 14-chlorodaunomycin and the remaining parts of the dissolved metal chloride are sufficient to cause the resultant 14-chlorodaunomycin acid-addition salt to be precipitated from the reaction solution by the salting-out process.

According to preferred embodiment of the process of the second aspect of this invention, the preparation of 14-chlorodaunomycin can be effected continuously and easily by employing the following procedures. Thus, daunomycin of the formula (II) or its acid addition salt is reacted with an alkyl orthoformate of formula (III) and a brominating agent in an organic solvent solution to form a 14-bromo-13-dialkylacetaldaunomycin of formula (IV) or its acid addition salt. Propylene oxide is then added to the resulting reaction mixture containing the compound of formula (IV) so that propylene oxide reacts with the by-produced hydrogen bromide present in the reaction mixture, whereby the hydrogen bromide is captured and eliminated. From the resulting reaction mixture, the organic solvent is distilled off to concentrate the reaction mixture. An other organic solvent (for example, isopropyl ether) incapable of dissolving the reaction product of formula (IV) is added to the concentrated reaction mixture, so that the compound of formula (IV) is caused to precipitate. The thus-precipitated compound of formula (IV) is recovered by filtration and is dissolved in a liquid mixture of the aforementioned inert organic solvent, preferably acetone, with an aqueous solution of an acid, whereby the acidic hydrolysis of the compound of the formula (IV) is performed with said acid in said liquid mixture to give 14-bromodaunomycin of formula (V). The resulting reaction solution containing 14-bromodaunomycin so produced is then washed with a water-immiscible organic solvent to remove therefrom the organic solvent which was employed in the hydrolysis reaction, and to remove the undesired reaction by-products. To the remaining aqueous solution thus-washed and containing 14-bromodaunomycin formula (V), is added in small portions an excess amount of an alkali metal chloride or alkaline earth metal chloride, preferably, sodium chloride or potassium chloride in the solid form, so that the metal chloride reacts with the compound of formula (V), to effect the halogen-interchange reaction, whereby the 14-bromo group of the compound of formula (V) is replaced by with a 14-chloro group, and at the same time, the salting-out of the 14-chlorodaunomycin of formula (I) is involved. As a result, the hydrochloride of 14-chlorodaunomycin of formula (I) is thus formed and obtained as a precipitate.

According to the process of the second aspect of this invention, the reaction steps for producing 14-chlorodaunomycin may be carried out in a continuous and facile way, and this process can readily afford the hydrochloride of 14-chlorodaunomycin of formula (I) in a favorably high yield of 73% or more as calculated from the starting hydrochloride of daunomycin of formula (II). When 14-chlorodaunomycin is used in the synthetic production of (2"R)-4'-O-THPADM of formula (A), the recovery and re-use of the undesired by-products as formed can be performed readily and effficiently so as to enable the (2"R)-4'-O-THPADM of formula (A) to be obtained in a favorable overall yield of 20.8% or more, as detailed hereinafter. This yield of 20.8% or more of (2"R)-4'-O-THPADM is a remarkable improvement as compared with such poor yield of (2"R)-4'-O-THPADM which is usually amounting to about 6 to 9% obtained when the prior art processes of the foresaid Japanese patent application first publication "Kokai" No. 104,299/80 or U.S. Pat. No. 4,303,785 and Japanese patent application first publication "Kokai" No. 156,300/81 or U.S. Pat. No. 4,360,664 are conducted. According to the first and second aspects of this invention, there are thus provided 14-chlorodaunomycin which is useful as an important intermediate compound for different derivatives of adriamycin, especially (2"R)-4'-O-THPADM, as well as a process of producing the 14-chlorodaunomycin.

Besides, we have further confirmed that 14-chlorodaunomycin according to this invention shows remarkable antitumor activity against various kinds of experimental tumors, as illustrated by the following tests, and that 14-chlorodaunomycin of this inventions may be used as an antitumor agent.

Antitumor activities of 14-chlorodaunomycin against various experimental tumors, including murine leukemia P-388 cells, murine leukemia P-388 cells (resistant to adriamycin), murine melanoma B16 cells, human lung cancer PC14 cells and murine leukemia L-1210 cells, were tested and evaluated in vitro by the following procedure:

The tumor cells were cultivated in RPMI 1640 medium supplemented with 10% fetal calf serum, $10\mu M$ 2-hydroxyethyldisulfide and kanamycin at 50 $\mu g/ml$ (the growth medium), under air containing 5% $CO_2$ at 37° C.

The tumor cells were incubated at initial densities of $1.5 \times 10^4$ cells/ml with murine melanoma B16; $2 \times 10^4$ cells/ml with murine leukemia P388, P388/ADR and L-1210; and $2.5 \times 10^4$ cells/ml with human lung cancer PC14 cells in the growth medium further containing graded concentrations of each test compound, for 72 hours. The $IC_{50}$ value, namely the 50% growth inhibitory concentration of the tested compound was evaluated by MTT assay method (see Mosmann, T; "J. Immunol. Methods", 65, 55–63 (1983).

TABLE 1

Antitumor activities (IC50 values, ng/ml) of 14-chlorodaunomycin against experimental tumors

| Test Compounds | IC50 value (ng/ml) Tumors | | | | |
| --- | --- | --- | --- | --- | --- |
| | P-388 | P-388 resistant to adriamycin | B16 | PC14 | L-1210 |
| 14-chlorodaunomycin | 96.3 | 552 | 93.0 | 960 | 268 |
| Daunomycin (comparative) | 16.3 | 668 | 44.9 | 237 | 65.5 |
| Adriamycin (comparative) | 33.0 | 2060 | 101 | 765 | 154 |

Furthermore, we, the present inventors, have found that 14-chlorodaunomycin as prepared newly by us is easy to handle as a starting material for a synthetic method of producing various anthracycline derivatives on an industrial scale, because, unlike 14-bromodaunomycin, 14-chlorodanomycin in a solid form undergoes no substantial decomposition even when it has been stored at $-10°$ C. for 1 week or so. It has also been uncovered that 14-chlorodaunomycin is somewhat stable even in its solution in an organic solvent and that even when the solution of 14-chlorodaunomycin in the organic solvent contains some water and an acidic compound, the decomposition rate of 14-chlorodaunomycin is considerably smaller than that of 14-bromodaunomycin which would be placed under the same conditions. We have also found that when the reaction stage of reacting 14-chlorodaunomycin with 3,4-dihydro-2H-pyran in a solution in an organic solvent in the presence of an acid catalyst to tetrahydropyranylate the 14-chlorodaunomycin is effected for the synthesis of (2″R)-4′-O-THPADM of formula (A), there is little danger of decomposition of the starting 14-chlorodaunomycin itself, even if no special care is exercised to maintain the reaction system in an extremely anhydrous state. The reaction stage for the tetrahydropyranylation of 14-chlorodaunomycin has hence now been found to have an advantage that it requires neither care nor faclities for maintaining the reaction system in an extremely anhydrous condition upon its commercial working and it can hence been worked out easily.

It has also been found that the resistance of the starting 14-chlorodaunomycin to decomposition in the reaction stage of its tetrahydropyranylation can contribute to give an improved yield of (2″R)-4′-O-THPADM of formula (A), the intended final antitumor compound.

According to a third aspect of this invention, there is thus provided a process for the preparation of (2″R)-4′-O-tetrahydropyranyladriamycin of formula (A)

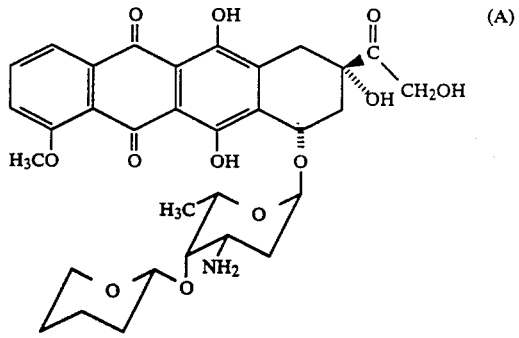

which comprises reacting 14-chlorodaunomycin of formula (I)

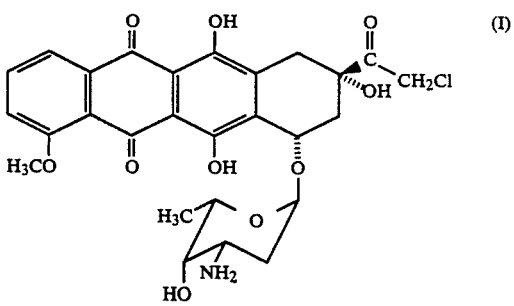

or an acid addition salt thereof with 3,4-dihydro-2H-pyran in the presence of an acid catalyst to tetrahydropyranylate the 4′-hydroxy group of 14-chlorodaunomycin, separating the resultant (2″R)-14-chloro-4′-O-tetrahydropyranyldaunomycin of formula (VI)

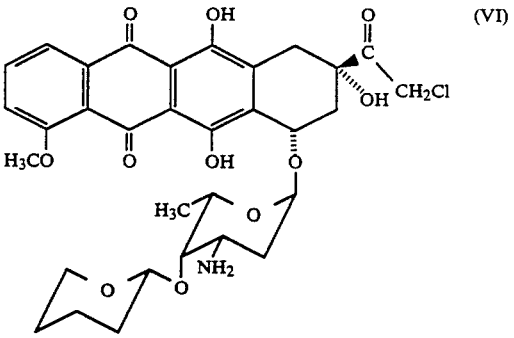

from the (2″S)-14-chloro-4′-O-tetrahydropyranyldaunomycin by-produced and also from the 14-chloro-9,4′-di-O-tetrahydropyranyldaunomycin by-produced, and then converting the 14-chloro group of the compound of formula (VI) into a 14-hydroxyl group to form the (2″R)-4′-O-tetrahydropyranyladriamycin of formula (A).

In a fourth aspect of this invention, there is provided a process for the preparation of (2″R)-4′-O-tetrahydropyranyladriamycin of formula (A).

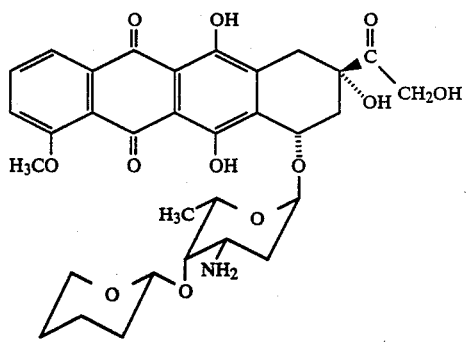

(A)

or an acid addition salt thereof, which comprises reacting 14-chlorodaunomycin of formula (I)

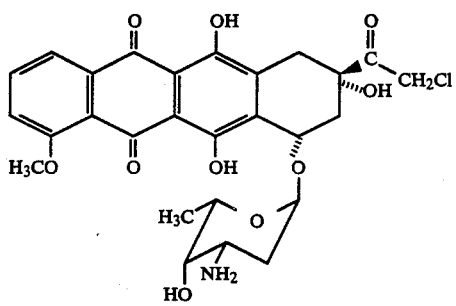

(I)

or an acid addition salt thereof with 3,4-dihydro-2H-pyran in the presence of an acid catalyst to tetrahydropyranylate the 4'-hydroxy group of 14-chlorodaunomycin, separating the resultant (2"R)-14-chloro-4'-O-tetrahydropyranyl-daunomycin of formula (VI)

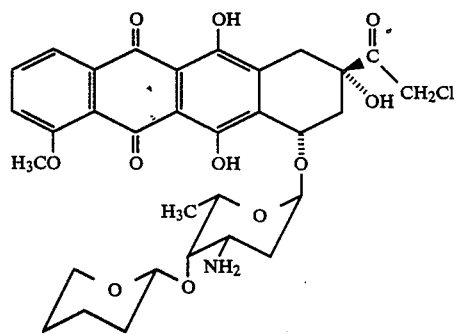

(VI)

from the (2"S)-14-chloro-4'-O-tetrahydropyranyl-daunomycin by-produced of formula (VII)

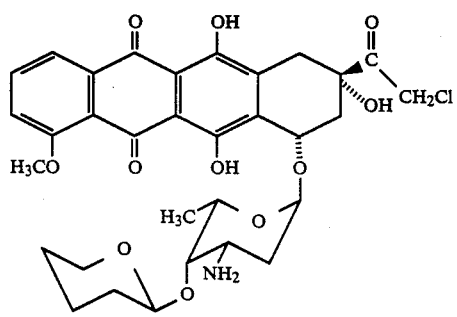

(VII)

and also from the 14-chloro-9,4'-di-O-tetrahydropyranyldaunomycin by-produced of formula (VIII)

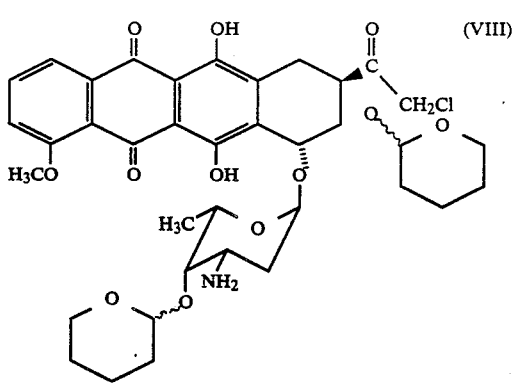

(VIII)

and then converting the 14-chloro group of the compound of formula (VI) into a 14-hydroxyl group to form (2"R)-4'-O-tetrahydropyranyladriamycin of formula (A)

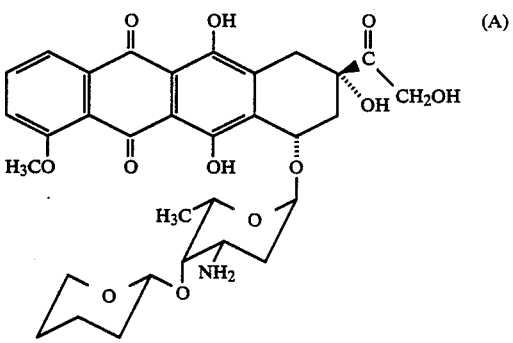

(A)

and recovering the by-produced (2"S)-14-chloro-4'-O-tetrahydropyranyldaunomycin of formula (VII) and 14-chloro-9,4'-di-O-tetrahydropyranyldaunomycin of formula (VIII), hydrolyzing the thus-recovered compound of formula (VII) and compound of the formula (VIII) under acidic conditions to regenerate 14-chlorodaunomycin, again tetrahydropyranylating the 4'-hydroxy group of the regenerated 14-chlorodaunomycin by reaction with 3,4-dihydro-2H-pyran in the presence of an acid catalyst, thereby to produce a second crop of the compound of formula (VI), and then converting the 14-chloro group of the second crop compound of formula (VI) into a 14-hydroxyl group so as to give a second crop of the (2"R)-4'-O-tetrahydropyranyladriamycin of formula (A).

The process according to the third aspect of this invention will hereinafter be described.

In the first step of the process according to the third aspect of this invention, 14-chlorodaunomycin of formula (I) or a salt thereof is reacted with 3,4-dihydro-2H-pyran in the presence of an acid catalyst in an organic solvent so as to tetrahydropyranylate the 4'-hydroxy group of 14-chlorodaunomycin. As exemplary solvents which are useful for this tetrahydropyranylation reaction, may be mentioned dimethylformamide, dimethylsulfoxide, methylene chloride, chloroform, tetrahydrofuran, dioxane, or a mixed solvent thereof. The reaction temperature may desirably range from 0° C. to 50° C., and the desirable reaction time may range from 1 hour to 72 hours. The acid catalyst employed in the stage of this tetrahydropyranylation reaction may be chosen suitably from organic sulfonic acids such as d-camphorsulfonic acid and p-toluenesulfonic acid, Lewis acids such as boron trifluoride, and mineral acids such as hydrochloric acid and sulfuric acid.

The reaction mixture obtained from the tetrahydropyranylation reaction contains the compound of formula (VI) formed as intended, along with the compound of formulae (VII) and (VIII) as by-produced. This reaction mixture is then neutralized with a mild alkali metal salt such as sodium hydrogencarbonate and then extracted with an immiscible organic solvent such as chloroform, whereby the compound of formula (VI), the compound of formula (VII) and the compound of formula (VIII) are extracted into the organic solvent employed as an extractant. The resulting extract solution containing these tetrahydropyranylated products (VI), (VII) and (VIII) is subjected to column chromatography on silica gel for the separation of these products, so that the principal product, namely, the intended (2"R)-14-chloro-4'-O-tetrahydropyranyldaunomycin of formula (VI), the by-produced (2"S)-14-chloro-4'-O-tetrahydropyranyldaunomycin of formula (VII) and 14-chloro-9,4'-di-O-tetrahydropyranyldaunomycin of formula (VIII) can be separated from one another.

Incidentally, when the unstable (2"R)-14-bromo-4'-O-tetrahydropyranyldaunomycin and (2"S)-14-bromo-4'-O-tetrahydropyranyldaunomycin which are formed in the prior art processes described hereinbefore are subjected to the step for the separation and purification of them by the column chromatography on silica gel in the same manner as described above, substantial portions of them can be decomposed (i.e., the cleavage of the amino sugar moiety from the aglycon) already in this step.

In the second step of the process according to the third aspect of this invention, the reaction is carried out to convert the 14-chloro group of the isolated compound of formula (VI) into a 14-hydroxyl group, and this reaction may be effected in a solution of the compound of formula (VI) dissolved in an organic solvent such as dimethylsulfoxide. The reaction for the conversion of 14-chloro group of the compound of formula (VI) into the 14-hydroxyl group may be carried out directly by hydrolyzing the compound (VI) with an alkali metal hydroxide or alkali metal carbonate. However, the reaction for converting the 14-chloro group of the compound (VI) into the 14-hydroxyl group may preferably be effected by a method which comprises reacting the compound of formula (VI) with an alkali metal salt or alkaline earth metal salt of an organic carboxylic acid represented by formula (IX):

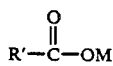

(IX)

wherein R' means a hydrogen atom or an alkyl or aralkyl group, preferably, a lower alkyl group and M denotes an alkali metal or alkaline earth metal, for example, preferably, an alkali metal or alkaline earth metal alkanoate, more preferably, lithium formate to give an ester compound of formula (X):

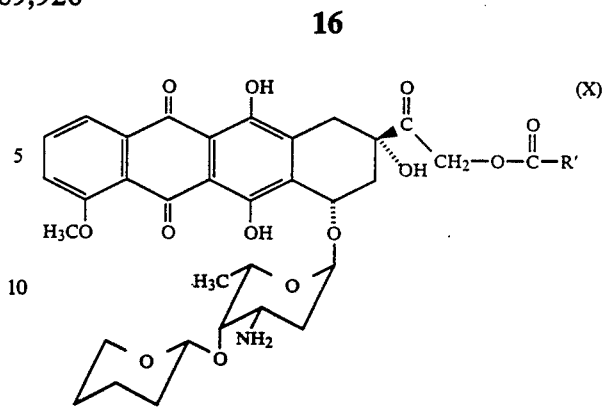

wherein R' means a hydrogen atom or an alkyl or aralkyl group, preferably, a lower alkyl group which was bonded to the carboxyl group of the carboxylic acid (IX) used, and then hydrolyzing the ester compound of formula (X) under alkaline conditions to afford the (2"R)-4'-O-tetrahydropyranyladriamycin of formula (A).

When (2"R)-14-chloro-4'-O-tetrahydropyranyldaunomycin of formula (VI) is esterified by reaction with an alkali metal salt of an organic carboxylic acid of formula (IX), for example, lithium formate, (2"R)-14-O-acyl-4'-O-tetrahydropyranyladriamycin of formula (X) are formed. As exemplary solvents which is useful for this esterification reaction, may be mentioned dimethylsulfoxide, dimethylformamide, ethers such as dioxane, tetrahydrofuran and dimethoxyethane, alkyl acetates, ketones such as acetone, and the like. The reaction temperature may desirably be 0°-50° C., and the desirable reaction time may range from 1 hour to 48 hours. Then hydrolysis of the ester compound of formula (X) is effected at 10°-40° C. in an inert solvent, for example, an ether such as tetrahydrofuran or dioxane, ketone such as acetone, dimethylformamide, dimethylsulfoxide or a mixed solvent thereof in the presence of an aqueous solution of sodium bicarbonate added, whereby (2"R)-4'-O-THPADM of formula (A) can be prepared.

In the process according to the fourth aspect of this invention, the reaction step for the tetrahydropyranylation of the compound of formula (I) and the reaction step for the conversion of the compound of formula (VI) into the desired compound of formula (A) may be practised in the same manner as in the corresponding reaction steps of the process according to the third aspect of this invention.

The compounds of formulae (VII) and (VIII) which have been by-produced in the first reaction step of the present process and separated chromatographically from the compound of formula (VI) can be converted into 14-chlorodaunomycin hydrochloride by dissolving them in an inert organic solvent and hydrolyzing them with a strong acid in the inorganic solvent, and the 14-chlorodaunomycin so regenerated can be recycled and re-used in the subsequent run of the synthesis of (2"R)-4'-O-THPADM. Illustrative examples of the inert organic solvent employed in the above hydrolytic reaction may include ethers such as tetrahydrofuran and dioxane, ketones such as acetone, dimethylsulfoxide, and N,N'-dimethylformamide. As the strong acid, an organic acid, especially, sulfonic acid or a mineral acid may be used.

According to the process of the fourth aspect of this invention, (2"R)-4'-O-tetrahydropiranyladriamycin of formula (A) can be obtained in a yield of 20.8% from daunomycin hydrochloride. The yield of (2"R)-4'-O-THPADM has thus been improved remarkedly, as compared with those available by the prior art processes (the yield amounted only to 6.9% by the process described in the Japanese Patent Application first publication "Kokai" No. 104,299/80; and 8.7% by the process described in the Japanese Patent Application first publication "Kokai" No. 156,300/81).

The (2"R)-4'-O-tetrahydropyranyladriamycin of formula (A) has not been obtained in any pure and crystalline product form according to the above-mentioned two known prior art processes, but the processes of the third and fourth aspects of this invention can make it possible that good purification of the (2"R)-4'-O-tetrahydropyranyladriamycin to give it as a pure crystalline product is achieved when the acidic water-extraction method with making use of a formic acid-sodium formate buffer solution is effected upon recovery and purification of the (2"R)-4-O-tetrahydropyranyladriamycin of formula (A). The present invention has therefore provided an improved process for preparing (2"R)-4'-O-tetrahydropyranyladriamycin of a high purity and in a high yield. This invention is now illustrated with reference to the following Examples, to which this invention is not limited.

EXAMPLE 1

Preparation of 14-chlorodaunomycin and its hydrochloride from daunomycin

Daunomycin hydrochloride (4.94 g) was dissolved in 50 ml of methanol and 50 ml of dioxane, and mixed with 4.4 ml of methyl orthoformate and 0.60 ml of bromine. The reaction solution was stirred at 10°–15° C. for 1 hour and then treated with 1.55 ml of propylene oxide. After 30 minutes at 4° C., the reaction mixture was concentrated to its one-fourth volume. The concentrate was poured into 530 ml of isopropyl ether and the red precipitate formed was collected by centrifugation, followed by washing with 70 ml of isopropyl ether.

185 ml of acetone and 180 ml of 0.25M hydrobromic acid were added to the precipitate, and the mixture was stirred for 2 days at room temperature. The reaction mixture was washed with 210 ml-portions of isopropyl ether three times under shaking, and the aqueous layer was separated. To the aqueous solution containing 14-bromodaunomycin hydrobromide was added solid sodium chloride (65 g) in small portions, and the precipitate formed was collected by centrifugation. The precipitate was twice washed with 20% aqueous solution of sodium chloride, collected by filtration and dried to give 5.0 g of red powder of crude 14-chlorodaunomycin hydrochloride.

The crude product of 14-chlorodaunomycin hydrochloride was dissolved in 235 ml of a 7% aqueous solution of sodium hydrogen carbonate, and the resultant 14-chlorodaunomycin (in the free base form) was extracted with 450 ml of methylene chloride, with 200 ml-portions of methylene chloride for three times, and further with 210 ml-portions of a mixed solvent of methylene chloride and methanol (6:1). The extracts were combined, dried over anhydrous sodium sulfate, and concentrated to 35 ml under reduced pressure. The concentrate was added dropwise to 180 ml of isopropyl ether, and the deposited 14-chlorodaunomycin (free base) was collected by filtration. Yield: 3.65 g.

Melting point: 174°–176° C. (decomposed).

Mass spectrum (FD): m/e 562(M+1)$^+$.

In 50 ml of a mixed solvent of methylene chloride and methanol (3:1) was dissolved 3.6 g of 14-chlorodaunomycin (free base) obtained above. Under ice-cooling the resultant solution, 6.4 ml of a solution of 1M-hydrogen chloride in methylene chloride was added gradually. The solution was added dropwise to isopropyl ether (280 ml) and the precipitate formed was collected and washed with isopropyl ether, thereby obtaining 3.83 g of 14-chlorodaunomycin hydrochloride. Yield: 73%.

Melting point: 166°–167° C.

NMR (D$_2$O,ppm)$\delta$: 1.35 (5'-methyl), 2.60–2.96 (10-methylene), 3.79 (3'-methine), 3.90 (4-o-methyl), 4.28 (5'-methine), 5.49 (1'-methine), 7.33 (2- and 3-methine), 7.60 (1-methine).

EXAMPLE 2

(a) Tetrahydropyranylation reaction of 14-chlorodaunomycin

14-Chlorodaunomycin hydrochloride (3.83 g) was dissolved in dry DMF (90 ml) and mixed with 18 ml of 3,4-dihydro-2H-pyran and pyridinium d-camphor-sulfonate (2.1 g) as catalyst. The mixture was stirred at 10° C. Each 4 ml-portions of 3,4-dihydro-2H-pyran and pyridinium d-camphorsulfonate (0.4 g) were added to the mixture at twenty hours and 29 hours later, respectively. After 44 hours, the reaction mixture was diluted with 180 ml of chloroform and washed with each 180 ml of 1% solution of sodium hydrogen carbonate twice.

The chloroform solution was further washed twice with 180 ml-portions of a 1% aqueous solution of sodium hydrogen carbonate, twice with 180 ml-portions of a 0.1% aqueous solution of sodium hydrogen carbonate and with water (100 ml), and was then dried over anhydrous sodium sulfate. The dried chloroform solution was chromatographed on a column of silica gel (250 g), using a mixed solvent of chloroform and methanol (70:1) as eluent. The eluate containing (2"R)-14-chloro-4'-O-tetrahydropyranyldaunomycin was concentrated to yield 958 mg of (2"R)-14-chloro-4'-O-tetrahydropyranyldaunomycin as red powder.

In addition, such fractions of the eluate containing (2"S)-14-chloro-4'-O-tetrahydropyranyldaunomycin and 14-chloro-9,4'-di-O-tetrahydropyranyldaunomycin were combined and concentrated to dryness, so that 3.23 g of a mixture of these by-products was recovered.

(b) Production of (2"R)-4'-O-tetrahydropyranyladriamycin

The (2"R)-14-chloro-4'-O-tetrahydropyranyladriamycin (200 mg) obtained in the procedure (a) of Example 2 was dissolved in dimethyl sulfoxide (6 ml) and mixed with lithium formate monohydrate (204 mg). The reaction mixture was stirred at room temperature for 5 hours. The mixture was diluted with ethyl acetate (35 ml) and washed with 35 ml of water. The organic layer was separated, washed four times with 30 ml-portions of water, and concentrated to an oil under reduced pressure.

The oil containing (2"R)-14-formyl-4'-O-tetrahydropyranyladriamycin was dissolved in tetrahydrofuran (6 ml), and treated with 2.4 ml of 0.1M solution of sodium hydrogen carbonate. The mixture was stirred at room temperature for 3.5 hours to conduct the hydrolytic reaction. Methylene chloride (50 ml) was added to the reaction mixture, and the solution was washed three times with 40 ml-portions of water. The methylene chloride solution was extracted with formate buffer (pH 3.3, 30 ml) in four portions.

An aqueous sodium hydroxide solution was added to adjust the pH of the combined buffer extracts to 7.5 and the product was extracted with methylene chloride (25 ml) in four portions. The methylene chloride extract, was dried over anhydrous sodium sulfate and concentrated to dryness to give 122 mg of (2"R)-4'-O-tetrahydropyranyladriamycin as a crude product. The crude product was crystallized from methylene chloride, followed by recrystallization from methylene chloride to afford 93 mg of (2"R)-4'-O-THPADM as a pure product.

Melting point: 184°-186° C. (decomposed).

$[\alpha]_D^{20}$: +210° (c 0.2, chloroform).

IR(in KBr):$\nu_{max}^{KBr}$ (cm$^{-1}$) 3460 (o-methyl and hydroxyl), 1720 (carbonyl), 1620 and 1580 (quinone).

$^1$H-NMR (CDCl$_3$) δ: 1.34 (5'-methyl), 1.45-1.87 (tetrahydropyranyl), 2.10-2.40 (8-methylene), 3.00 (3'-methine), 3.00-3.31 (10-methylene), 3.67 (4'-methine), 3.98-4.05 (5'-methine), 4.09 (4-o-methyl), 4.71 (2"-methine, anomeric of tetrahydropyranyl), 4.75 (14-methylene), 5.32 (7-methine), 5.52 (1'-methine), anomeric of daunosamine), 7.40 (3-methine), 7.79 (2-methine), 8.04 (1-methine).

With subtracting the yield of 14-chlorodaunomycin hydrochloride which was recovered in Example 3 given below, the yield of (2"R)-4'-O-THPADM was calculated as amounting to 28% as based on the 14-chlorodaunomycin hydrochloride consumed.

EXAMPLE 3

Recovery of 14-chlorodaunomycin hydrochloride 3.23 g of the mixture of the by-products which was obtained in the procedure (a) of Example 2 was dissolved in 80 ml of a (1:1) mixed solvent of acetone and 0.25M hydrobromic acid. The resultant solution was stirred at room temperature for 30 hours to regenerate 14-chlorodaunomycin. The reaction mixture was washed with 45 ml-portions of isopropyl ether for three times, and the aqueous layer was separated. Sodium chloride (14 g) was added to the aqueous solution of 14-chlorodaunomycin and the red precipitate formed was washed with a 20% solution of sodium chloride to give a crude product, which was purified in accordance with the method described in the Example 1 above, to afford 2.34 g of 14-chlorodaunomycin hydrochloride as a powder.

Melting point: 165°-166° C.

Mass spectrum (FD) (as free base): m/e 562 (M+1)$^+$.

$^1$H-NMR spectrum of the regenerated 14-chlorodaumycin hydrochloride was identical to that of the 14-chlorodaunomycin hydrochloride which was obtained in the Example 1 above. Therefore, 2.34 g-portion of the starting 14-chlorodaunomycin hydrochloride (3.83 g) used in the procedure (a) of Example 2 was recovered from the by-products of the tetrahydropyranylation step (the recovered yield: 61%).

We claim:

1. A process for the preparation of 14-chlorodaunomycin of the formula (I)

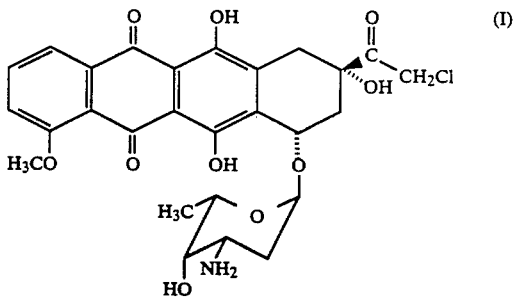

or an acid addition salt thereof, which comprises reacting daunomycin of formula (II)

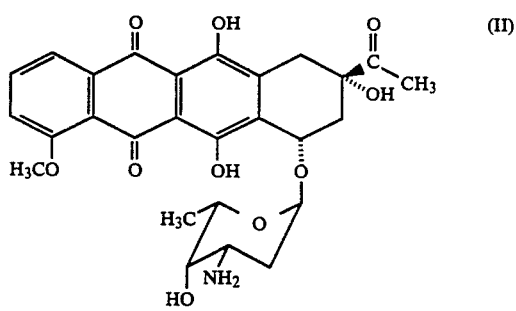

or an acid addition salt thereof with an alkyl ortho-formate of formula (III)

wherein R is a lower alkyl group, and a brominating agent in solution in an organic solvent to form 14-bromo-13-dialkylketaldaunomycin of formula (IV)

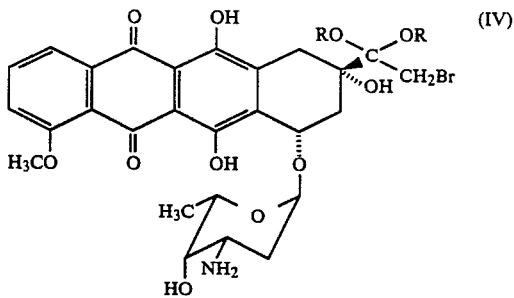

wherein R is as defined above, or an acid addition salt thereof, hydrolyzing the compound of formula (VI) by treating with an aqueous solution of an acid under acidic conditions, then adding an excess amount of solid metal chloride to the resulting aqueous reaction mixture containing the acid-addition salt of 14-bromodaunomycin so produced and represented by formula (V)

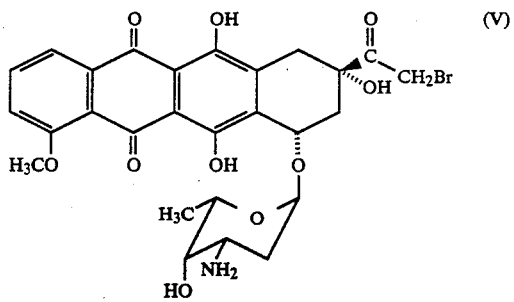

to dissolve the solid metal chloride into said aqueous reaction mixture and to react the dissolved metal chloride with 14-bromodaunomycin acid-addition salt so that the 14-bromo group of 14-bromodaunomycin of formula (V) undergoes the halogen-exchange reaction with the metal chloride to produce the acid-addition salt of 14-chlorodaunomycin of formula (I) and concurrently allowing the acid-addition salt of the 14-chlorodaunomycin of formula (I) to be precipitated from the resulting aqueous reaction solution by the salting-out of the 14-chlorodaunomycin acid-addition salt, the amount of said solid metal chloride being such that a part of the metal chloride as dissolved from the added solid metal chloride into said aqueous reaction mixture is sufficient to convert all the 14-bromodaunomycin present into the 14-chlorodaunomycin and the remaining parts of the dissolved metal chloride are sufficient to cause the resultant 14-chlorodaunomycin acid-addition salt to be precipitated from the reaction solution by the salting-out process, and recovering the acid-addition salt of 14-chlorodaunomycin from the aqueous reaction solution, and when desired, treating the recovered 14-chlorodaunomycin acid-addition salt with an aqueous alkaline compound under weakly alkaline conditions to afford 14-chlorodaunomycin in its free base form.

2. The process as claimed in claim 1, wherein the metal chloride used is an alkali metal chloride and preferably is sodium chloride or potassium chloride.

3. The process as claimed in claim 1, wherein daunomycin of formula (II) or the acid addition salt thereof is reacted with the alkyl orthoformate of formula (III) and the brominating agent in the organic solvent solution to form the 14-bromo-13-dialkylketaldaunomycin of formula (IV) or the acid addition salt thereof, propylene oxide is added to the resulting reaction mixture containing the compound of formula (IV) so produced, so that the propylene oxide reacts with the by-produced hydrogen bromide present in the reaction mixture to capture and eliminate the hydrogen bromide from the reaction mixture, and wherein the organic solvent is then distilled off from the resultant reaction mixture to concentrate the reaction mixture, an organic solvent incapable of dissolving the compound of formula (IV) is added to the concentrated reaction mixture so that the compound of formula (IV) is caused to precipitate, the compound of the formula (IV) thus precipitated is recovered and then dissolved in a liquid mixture of an inert organic solvent with an aqueous solution of an acid, whereby the compound of formula (IV) is hydrolyzed with the aqueous acid in said liquid mixture to give the aqueous reaction solution containing 14-bromodaunomycin of formula (V) as formed, and wherein said aqueous reaction solution is washed with a water-immiscible organic solvent, and the organic solvent phase is removed from said reaction solution, followed by adding an excess amount of a solid alkali metal chloride or alkaline earth metal chloride, preferably, solid sodium chloride or potassium chloride in small portions to the remaining aqueous solution of the compound of formula (V) as obtained from the washing step, so that the alkali metal chloride or alkaline earth metal chloride, preferably, sodium chloride or potassium chloride is dissolved into the aqueous solution and then reacted with the compound of formula (V) so as to effect the halogen-interchange reaction, whereby the 14-bromo group of the compound of formula (V) is replaced by the 14-chloro group, and at the same time the salting-out and precipitation of the hydrochloride of the resulting 14-chlorodaunomycin of formula (I) are involved.

4. A process for the preparation of (2″R)-4′-O-tetrahydropyranyladriamycin of formula (A)

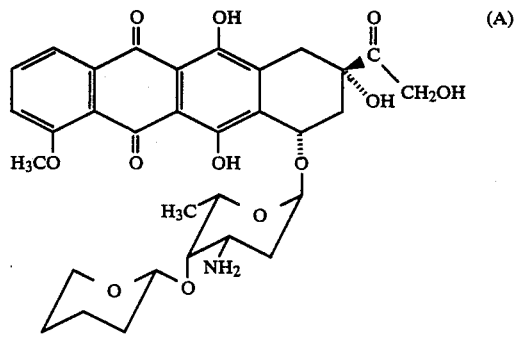

which comprises reacting 14-chlorodaunomycin of formula (I)

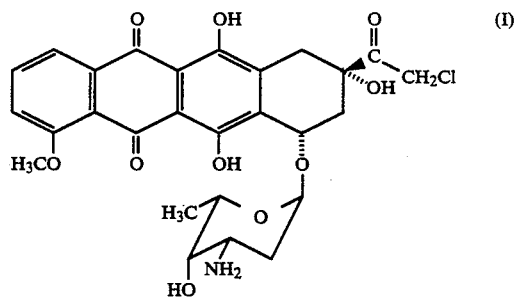

or an acid addition salt of 14-chlorodaunomycin, with 3,4-dihydro-2H-pyran in the presence of an acid catalyst to tetrahydropyranylate the 4′-hydroxy group of 14-chlorodaunomycin, separating chromatographically on a column of silica gel the resultant (2″R)-14-chloro-4′-O-tetrahydropyranyldaunomycin of formula (VI)

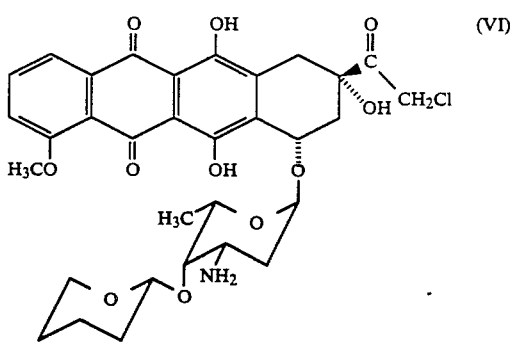

from the (2″S)-14-chloro-4′-O-tetrahydropyranyl-daunomycin by-produced and also from the 14-chloro-9,4′-di-O-tetrahydropyranyldaunomycin by-produced, and then converting the 14-chloro group of the compound of formula (VI) into a 14-hydroxyl group to form the (2″R)-4′-O-tetrahydropyranyladriamycin of formula (A).

5. A process for the preparation of (2″R)-4′-O-tetrahydropyranyladriamycin of formula (A)

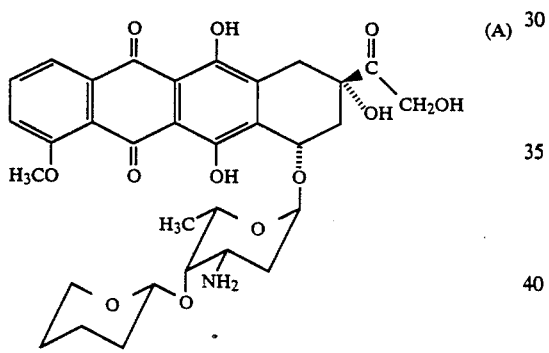

or an acid addition salt thereof, which comprises reacting 14-chlorodaunomycin of formula (I)

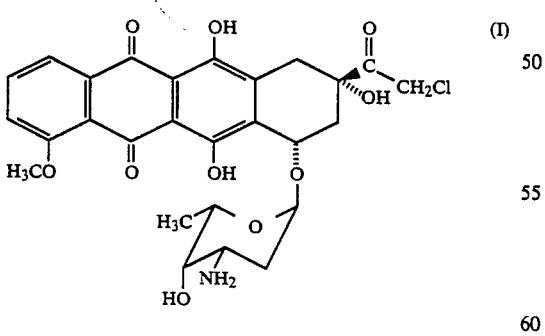

or an acid addition salt of 14-chlorodaunomycin, with 3,4-dihydro-2H-pyran in the presence of an acid catalyst to tetrahydropyranylate the 4′-hydroxy group of 14-chlorodaunomycin, separating chromatographically on a column of silica gel the resultant (2″R)-14-chloro-4′-O-tetrahydropyranyldaunomycin of formula (VI)

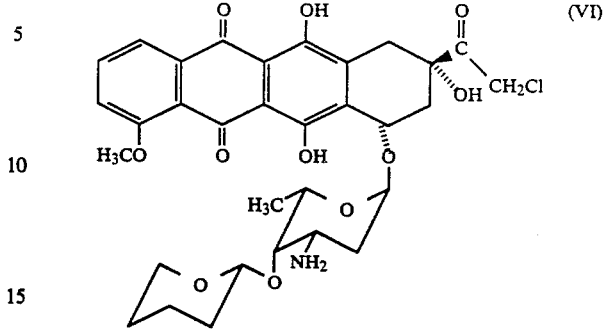

from the (2″S)-14-chloro-4′-O-tetrahydropyranyl-daunomycin by-produced of formula (VII)

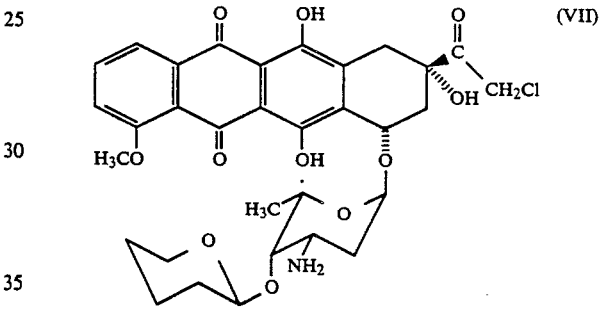

and also from the 14-chloro-9,4′-di-O-tetrahydropyranyldaunomycin by-produced of formula (VIII)

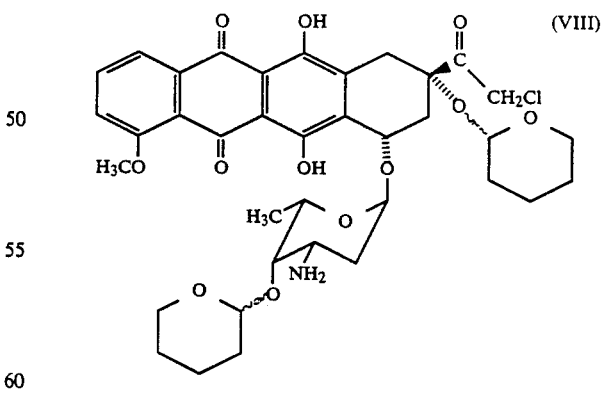

and then converting the 14-chloro group of the compound of formula (VI) into a 14-hydroxyl group to form (2″R)-4′-O-tetrahydropyranyladriamycin of formula (A).

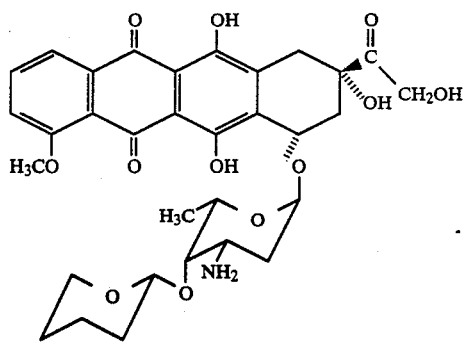

(A)

and recovering the by-produced (2″S)-14-chloro-4′-O-tetrahydropyranyldaunomycin of formula (VII) and 14-chloro-9,4-di-O-tetrahydropyranyldaunomycin of formula (VIII), hydrolyzing the thus-recovered compound of formula (VII) and compound of the formula (VIII) under acidic conditions to regenerate 14-chlorodaunomycin, again tetrahydropyranylating the 4′-hydroxy group of the regenerated 14-chlorodaunomycin by reaction with 3,4-dihydro-2H-pyran in the present of an acid catalyst, thereby to produce a second crop of the compound of formula (VI), and then converting the 14-chloro group of the second crop compound of formula (VI) into a 14-hydroxyl group so as to give a second crop of the (2″R)-4′-O-tetrahydropyranyladriamycin of formula (A).

6. The process as claimed in claim 4, wherein the reaction for converting the 14-chloro group of the compound of formula (VI) into the 14-hydroxyl group comprises hydrolyzing the compound of formula (VI) directly with an alkali metal hydroxide or carbonate.

7. The process as claimed in claim 4, wherein the reaction for converting the 14-chloro group of the compound of formula (VI) into the 14-hydroxyl group comprises reacting the compound of formula (VI) with an alkali metal or alkaline earth metal salt of an organic carboxylic acid of formula (IX)

(IX)

wherein R′ means a hydrogen atom or an alkyl or aralkyl group, preferably, a lower alkyl group, and M denotes an alkali metal or alkaline earth metal, preferably, an alkali metal or alkaline earth metal alkanoate, more preferably, lithium formate to give an ester compound of formula (X)

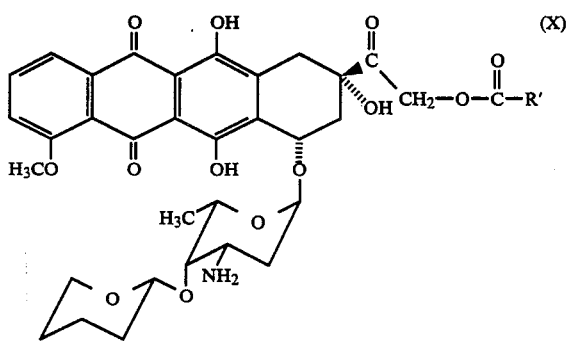

(X)

wherein R′ means a hydrogen atom or an alkyl or aralkyl group, preferably, a lower alkyl group which was bonded to the carboxyl group of the carboxylic acid (IX) used, and then hydrolyzing the ester compound of formula (X) under alkaline conditions to afford (2″R)-4′-O-tetrahydropyranyladrimycin of formula (A).

* * * * *